United States Patent
Demenezes

[11] Patent Number: 6,007,477
[45] Date of Patent: Dec. 28, 1999

[54] EYE TREATMENT DEVICE

[76] Inventor: Jose E. Demenezes, 303 14th Ave., Indian Rocks Beach, Fla. 33785

[21] Appl. No.: 09/022,361

[22] Filed: Feb. 12, 1998

[51] Int. Cl.$^6$ ..................................................... A61N 1/00
[52] U.S. Cl. ................................................................ 600/13
[58] Field of Search ........................................... 600/9–15

[56] References Cited

U.S. PATENT DOCUMENTS

| | | |
|---|---|---|
| 3,902,502 | 9/1975 | Liss et al. . |
| 4,155,366 | 5/1979 | Di Mucci . |
| 4,271,841 | 6/1981 | Friedman . |
| 4,614,193 | 9/1986 | Liss et al. . |
| 4,628,933 | 12/1986 | Michelson . |
| 4,940,453 | 7/1990 | Cadwell .................................. 600/13 |
| 5,067,940 | 11/1991 | Liboff et al. ........................... 600/13 |

Primary Examiner—John P. Lacyk

[57] ABSTRACT

A device for reducing the internal pressure of an eyeball is provided with a power source and a pair of contacts for generating a current within an eyeball. Also included is at least one inductor coil assembly connected to the power source and having an inductive coil for being situated against an eyeball of a user thereby generating a magnetic field for treating the eyeball.

6 Claims, 1 Drawing Sheet

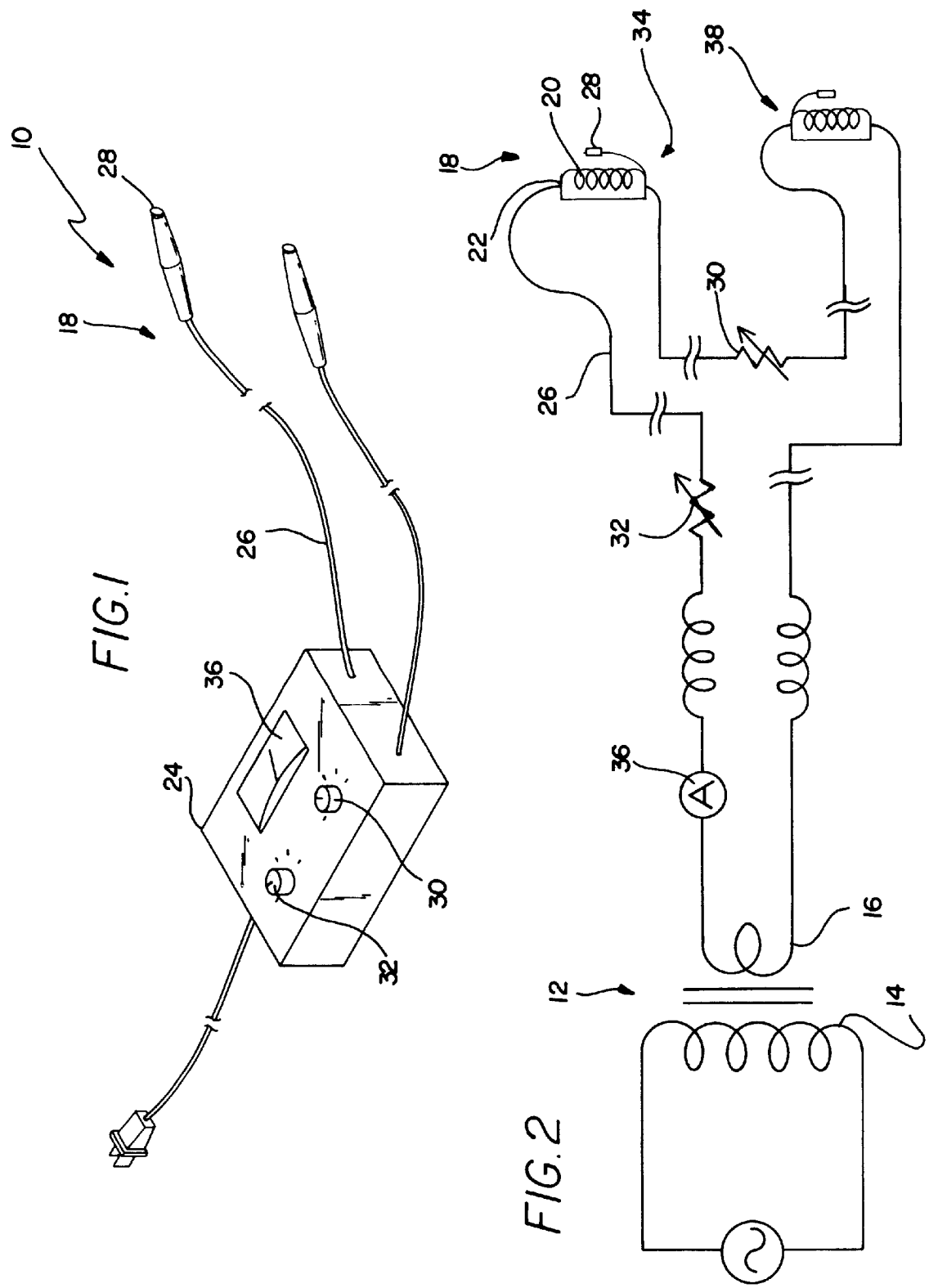

EYE TREATMENT DEVICE

BACKGROUND OF THE INVENTION

1. Field of the Invention

The present invention relates to electronic treatments and more particularly pertains to a new eye treatment device for reducing the internal pressure within an eyeball.

2. Description of the Prior Art

The use of electronic treatments is known in the prior art. More specifically, electronic treatments heretofore devised and utilized are known to consist basically of familiar, expected and obvious structural configurations, notwithstanding the myriad of designs encompassed by the crowded prior art which have been developed for the fulfillment of countless objectives and requirements.

Known prior art electronic treatments include U.S. Pat. No. 4,614,193; U.S. Pat. No. 4,271,841; U.S. Pat. No. 4,628,933; U.S. Pat. No. Des. 264,243; U.S. Pat. No. 3,902,502; and U.S. Pat. No. 4,155,366.

In these respects, the eye treatment device according to the present invention substantially departs from the conventional concepts and designs of the prior art, and in so doing provides an apparatus primarily developed for the purpose of reducing the internal pressure of an eyeball.

SUMMARY OF THE INVENTION

In view of the foregoing disadvantages inherent in the known types of electronic treatments now present in the prior art, the present invention provides a new eye treatment device construction wherein the same can be utilized for reducing the internal pressure of an eyeball.

The general purpose of the present invention, which will be described subsequently in greater detail, is to provide a new eye treatment device apparatus and method which has many of the advantages of the electronic treatments mentioned heretofore and many novel features that result in a new eye treatment device which is not anticipated, rendered obvious, suggested, or even implied by any of the prior art electronic treatments, either alone or in any combination thereof.

To attain this, the present invention generally comprises a step down transformer having a primary coil connected to a high power alternating current source. Associated therewith is a secondary coil for providing a low power alternating current source. Next provided is a pair of inductor coil assemblies each having an inductive coil wound about an iron cylindrical post. The inductive coil and post of each inductor coil assembly are lined with a thin elastomeric lining, as shown in FIG. 1. Mounted on an end of each one of the inductor coil assemblies is a contact electrically connected to the inductive coil thereof. A first rheostat is electrically connected between the contacts. Also included is a second rheostat connected to the inductive coil of a first one of the inductor coil assemblies. An ammeter is connected between the secondary coil of the transformer and the second rheostat. The inductive coil of a second one of the inductor coil assemblies is also connected to the secondary coil of the transformer thereby rendering a series circuit. In operation, alternating current flows through the inductive coils of the inductor coil assemblies. Upon the depression of one of the contacts against an eye ball of a user and another one of the contacts against another part of the user, a parallel circuit is defined along the series circuit. Such parallel circuit includes a resistivity of the user and the first rheostat. As such, the alternating current flows through the eyeball of the user. Further, a magnetic field is applied to the eye ball for treating the same. By the specific interconnection of the contacts with respect to the inductive coils, upon each cycle of the current, such current flows through one of the inductive coils prior to entering the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new eye treatment device apparatus and method which has many of the advantages of the electronic treatments mentioned heretofore and many novel features that result in a new eye treatment device which is not anticipated, rendered obvious, suggested, or even implied by any of the prior art electronic treatments, either alone or in any combination thereof.

It is another object of the present invention to provide a new eye treatment device which may be easily and efficiently manufactured and marketed.

It is a further object of the present invention to provide a new eye treatment device which is of a durable and reliable construction.

An even further object of the present invention is to provide a new eye treatment device which is susceptible of a low cost of manufacture with regard to both materials and labor, and which accordingly is then susceptible of low prices of sale to the consuming public, thereby making such eye treatment device economically available to the buying public.

Still yet another object of the present invention is to provide a new eye treatment device which provides in the apparatuses and methods of the prior art some of the advantages thereof, while simultaneously overcoming some of the disadvantages normally associated therewith.

Still another object of the present invention is to provide a new eye treatment device for reducing the internal pressure of an eyeball.

Even still another object of the present invention is to provide a new eye treatment device that includes a power source and a pair of contacts for generating a current within an eyeball. Also included is at least one inductor coil assembly connected to the power source and having an inductive coil for being situated against an eyeball of a user thereby generating a magnetic field for treating the eyeball.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new eye treatment device according to the present invention.

FIG. 2 is a schematic diagram of the present invention.

DESCRIPTION OF THE PREFERRED EMBODIMENT

With reference now to the drawings, and in particular to FIGS. 1 and 2 thereof, a new eye treatment device embodying the principles and concepts of the present invention and generally designated by the reference numeral 10 will be described.

The present invention, designated as numeral 10, includes a step down transformer 12 having a primary coil 14 connected to a high power alternating current source. Associated therewith is a secondary coil 16 for providing a low power alternating current source.

Next provided is a pair of inductor coil assemblies 18 each having an inductive coil 20 wound about an iron cylindrical post 22. The inductive coil and post of each inductor coil assembly are lined with a thin generally cylindrical elastomeric lining, as shown in FIG. 1. In the preferred embodiment, the inductor coil assemblies are each housed separately from each other and further separate from the remaining components of the present invention. Every component of the present invention, with the exception of the inductor coil assemblies are housed within a box 24. The inductor coil assemblies are connected to the components with the box via a pair of double stranded wires 26.

Mounted on an end of each one of the inductor coil assemblies is a contact 28 electrically connected to an end of the inductive coil thereof. As shown in FIG. 1, each contact is physically mounted exterior of the elastomeric lining on an end of the inductive coil opposite that from which the elongated wires 26 extend.

A first rheostat 30 is situated within the box and electrically connected between the contacts. Also included is a second rheostat 32 connected to the inductive coil of a first one of the inductor coil assemblies 34. An ammeter 36 is connected between the secondary coil of the transformer and the second rheostat. The inductive coil of a second one of the inductor coil assemblies 38 is also connected to the secondary coil of the transformer thereby rendering a series circuit. As an option, additional inductive coils may be connected along the series circuit, as shown in FIG. 2.

In operation, alternating current flows through the inductive coils of the inductor coil assemblies. Upon the depression of one of the contacts against an eye ball of a user and another one of the contacts against another part of the user, a parallel circuit is defined along the series circuit. Such parallel circuit includes a resistivity of the user and the first rheostat. As such, the alternating current flows through the eyeball of the user. Further, a magnetic field is applied to the eye ball for treating the same. By the specific interconnection of the contacts with respect to the inductive coils, upon each cycle of the alternating current, such current flows through one of the inductive coils prior to entering the user.

It should be understood that the alternating current and magnetic field are adjusted and monitored via the rheostats and ammeter, respectively. As shown in FIG. 1, dials and a display associated with the rheostats and ammeter, respectively, are included for such purpose.

In use, conduction currents from the contacts are regulated to a level of approximately 1.5 mA AC from approximately 10–30 Volts RMS. As such, a reduction of pressure from accumulation of excess aqueous humor is accomplished by way of a combination of electrolysis and exposure to non-ionizing electromagnetic fields. In the basic theory of operation, the electrolysis of the aqueous humor is used to break down the larger molecules into smaller ions that can more readily migrate through cellular barriers in the eye. The simultaneous exposure to non-ionizing, near-field electromagnetic radiation is then effected to provide a means of ion alignment and movement along the electromagnetic field lines to induce a reduction in aqueous humor pressure of the eye under treatment. Options capable of being incorporated with the present invention include a ground fault interrupter provision, an isolation transformer, precision low-voltage/current control and the like.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A device for reducing the internal pressure of an eyeball comprising, in combination:

a step down transformer including a primary coil connected to a high power alternating current source and a secondary coil for providing a low power alternating current source;

a pair of inductor coil assemblies each having an inductive coil wound about an iron cylindrical post, the inductive coil and post of each inductor coil assembly being lined with a thin elastomeric lining;

a pair of contacts each mounted on an end of an associated one of the inductor coil assembly and further electrically connected to the inductive coil thereof;

a first rheostat electrically connected between the contacts; and a second rheostat connected to the inductive coil of a first one of the inductor coil assemblies;

an ammeter connected between the secondary coil of the transformer and the second rheostat, wherein the inductive coil of a second one of the inductor coil assemblies is also connected to the secondary coil of the transformer thereby rendering a series circuit;

whereby alternating current flows through the inductive coils of the inductor coil assemblies and upon the depression of the contacts against an eye ball of a user, a parallel circuit is defined along the series circuit which includes a resistivity of the user and the first rheostat, thereby applying a magnetic field and alternating current to the eye ball for treating the same, wherein the alternating current and magnetic field is adjusted and monitored via the rheostats and ammeter, respectively.

2. A device for reducing the internal pressure of an eyeball comprising:

a power source;

a pair of inductor coil assemblies connected to the power source, each inductor coil assembly having an inductive coil electrically connected to a contact mounted on an end of the inductive coil assembly, the contact being adapted for situating against an eyeball of a user thereby generating a magnetic field for treating the eyeball.

3. A device for reducing the internal pressure of an eyeball as set forth in claim 2 including a rheostat, wherein the current available for flowing through the contact and through a user is controlled by means of the rheostat.

4. A device for reducing the internal pressure of an eyeball as set forth in claim 2 wherein inductive coils of the inductor coil assemblies each have a contact adapted for situating against the eyeball of a user, each contact being connected to the respective inductive coil for allowing current to flow through the eyeball of a user.

5. A method for reducing the internal pressure of an eyeball comprising:

providing a device comprising at least one inductor coil assembly adapted for connection to a power source, each inductor coil assembly having an inductive coil electrically connected to a contact mounted on an end of the inductive coil assembly, the contact being for situating against an eyeball of a user for thereby generating a magnetic field for treating the eyeball; and subjecting the eyeball to a magnetic field.

6. A method for reducing the internal pressure of an eyeball as set forth in claim 5, and further including the step of effecting a current flow through the eyeball.

\* \* \* \* \*